(12) United States Patent
Borbely et al.

(10) Patent No.: US 7,976,825 B2
(45) Date of Patent: Jul. 12, 2011

(54) CANCER CELL DIAGNOSIS BY TARGETING DELIVERY OF NANODEVICES

(76) Inventors: Janos Borbely, Debrecen (HU); Magdolna Bodnar, Hajouboszormeny (HU); John F Hartmann, Princeton Junction, NJ (US); Istvan Hajdu, Tiszacsege (HU); Jozsef Kollar, Debrecen (HU); Gyorgy Vamosi, Debrecen (HU)

( * ) Notice: Subject to any disclaimer, the term of this patent is extended or adjusted under 35 U.S.C. 154(b) by 0 days.

(21) Appl. No.: 12/315,951

(22) Filed: Dec. 8, 2008

(65) Prior Publication Data

US 2009/0180966 A1    Jul. 16, 2009

Related U.S. Application Data

(60) Provisional application No. 61/005,646, filed on Dec. 6, 2007.

(51) Int. Cl.
  *A61B 5/055*    (2006.01)
  *A61B 49/04*    (2006.01)
  *A61K 9/50*    (2006.01)

(52) U.S. Cl. .................... 424/9.323; 424/9.35; 424/9.43; 424/493; 424/497; 424/499; 977/773; 977/930

(58) Field of Classification Search .................... None
See application file for complete search history.

(56) References Cited

U.S. PATENT DOCUMENTS

| | | | | |
|---|---|---|---|---|
| 5,820,851 A | * | 10/1998 | Peng et al. | 424/9.361 |
| 7,291,598 B2 | * | 11/2007 | Sung et al. | 514/12 |
| 2005/0226938 A1 | * | 10/2005 | Borbely et al. | 424/492 |
| 2008/0160096 A1 | * | 7/2008 | Berbely et al. | 424/493 |

FOREIGN PATENT DOCUMENTS

| WO | WO 00/66090 | * 11/2000 |
|---|---|---|
| WO | WO 2004096998 | * 11/2004 |

\* cited by examiner

*Primary Examiner* — Richard Schnizer
(74) *Attorney, Agent, or Firm* — Thomas A. O'Rourke; Bodner & O'Rourke, LLP

(57) ABSTRACT

Macromolecular contrast agents for magnetic resonance imaging are described. Biomolecules and their modified derivatives form stable complexes with paramagnetic ions thus increasing the molecular relaxivity of carriers. The synthesis of biomolecular based nanodevices for targeted delivery of MRI contrast agents are described. Nanoparticles (NP) have been constructed by self-assembling of chitosan (CHIT) as polycation and poly-gamma glutamic acids (PGA) as polyanion. NP's are capable of Gd-ion uptake forming a particle with suitable molecular relaxivity. Folic acid (FA) is linked to the NP's to produce NP-FA bioconjugates that can be used for targeted in vitro delivery to a human cancer cell line.

23 Claims, 1 Drawing Sheet

A

B

CANCER CELL DIAGNOSIS BY TARGETING DELIVERY OF NANODEVICES

This application claims priority on U.S. Provisional Patent Application 61/005,646, filed Dec. 6, 2007 and is a continuation-in-part of U.S. patent application Ser. No. 12/005,643 filed Dec. 27, 2007 the disclosures of which are hereby incorporated by reference.

FIELD OF INVENTION

The present invention relates to biocompatible and biodegradable stimuli sensitive polymeric nanoparticles. More particularly, the present invention relates to nanoparticles useful as contrast agents for magnetic resonance imaging.

BACKGROUND OF THE INVENTION

Magnetic resonance imaging (MRI) is an imaging technique used primarily in the medical field to produce high quality images of the inside of the human body. MRI's are based on a spectroscopic technique used to obtain microscopic chemical and physical information about molecules. MRI's started as a tomographic imagery technique that produced an image of the nuclear magnetic resonance signal in a thin slice through the human body. MRI's have advanced past tomographic imaging to a volume imaging technique.

Magnetic resonance imaging (MRI), uses a powerful magnetic field to align the nuclear magnetization of, for example hydrogen atoms in water in the body. Radiofrequency fields are used to systematically alter the alignment of this magnetization, causing the hydrogen nuclei to produce a rotating magnetic field detectable by the scanner. This signal can be manipulated by additional magnetic fields to build up enough information to construct an image of the body. When a patient goes inside the powerful magnetic field of the scanner these protons align with the direction of the field.

A second radiofrequency electromagnetic field is then briefly turned on causing the protons to absorb some of its energy. When this field is turned off the protons release this energy at a radiofrequency which can be detected by the scanner. The position of protons in the body can be determined by applying additional magnetic fields during the scan which allows an image of the body to be built up. These are created by turning gradients coils on and off which creates the familiar knocking sounds during an MR scan.

Diseased tissue, such as tumors, can be detected because the protons in different tissues return to their equilibrium state at different rates. By changing the parameters on the scanner this effect is used to create contrast between different types of body tissue. Contrast agents may be injected intravenously to enhance the appearance of blood vessels, tumors or inflammation. Contrast agents may also be directly injected into a joint, in the case of arthrograms, MR images of joints.

Image contrast is created by differences in the strength of the NMR signal recovered from different locations within the sample. This depends upon the relative density of excited nuclei (usually water protons), on differences in relaxation times ($T_1$, $T_2$ and $T_2^*$) of those nuclei after the pulse sequence, and often on other parameters.

Contrast in most MR images is actually a mixture of all these effects, but careful design of the imaging pulse sequence allows one contrast mechanism to be emphasized while the others are minimized. In some situations it is not possible to generate enough image contrast to adequately show the anatomy or pathology of interest by adjusting the imaging parameters alone, in which case a contrast agent may be administered. This can be as simple as water, taken orally, for imaging the stomach and small bowel. However, most contrast agents used in MRI are selected for their specific magnetic properties. Most commonly, a paramagnetic contrast agent (usually a gadolinium compound)

There have been concerns raised recently regarding the toxicity of gadolinium-based contrast agents and their impact on persons with impaired kidney function. The American College of Radiology released screening criteria for patients intended to be given Gadolinium-based contrast agents to identify potential risk factors for negative reactions. Special actions may be taken, such as hemodialysis following a contrast MRI scan for renally-impaired patients. More recently, superparamagnetic contrast agents (e.g. iron oxide nanoparticles) have become available. These agents appear very dark on $T_2^*$-weighted images and may be used for liver imaging, as normal liver tissue retains the agent, but abnormal areas (e.g. scars, tumors) do not. They can also be taken orally, to improve visualization of the gastrointestinal tract, and to prevent water in the gastrointestinal tract from obscuring other organs (e.g. pancreas). Diamagnetic agents such as barium sulfate have also been studied for potential use in the gastrointestinal tract, but are less frequently used.

Paramagnetic contrast agents have been demonstrated to provide clinical effectiveness in MRI's. The capacity to differentiate regions/tissues that may be magnetically similar but histologically distinct is a major impetus for the preparation of these agents. In the design of MRI agents, attention must be given to a variety of properties that will ultimately effect the physiological outcome apart from the ability to provide contrast enhancement. Two fundamental properties that must be considered are biocompatability and proton relaxation enhancement. Biocompatability is influenced by several factors including toxicity, stability (thermodynamic and kinetic), pharmacokinetics and biodistribution. Proton relaxation enhancement (or relaxivity) is chiefly governed by the choice of metal and rotational correlation times.

Paramagnetic metal ions, as a result of their unpaired electrons, act as potent relaxation enhancement agents. They decrease the T, and T2 relaxation times of nearby (independence) spins. Some paramagnetic ions decrease the T, without causing substantial linebroadening (e.g. gadolinium (III), (Gd3+)), while others induce drastic linebroadening (e.g. superparamagnetic iron oxide). The lanthanide atom, Gd3+, is by the far the most frequently chosen metal atom for MRI contrast agents because it has a very high magnetic moment (u1=63BM2), and a symmetric electronic ground state, (S8). Transition metals such as high spin Mn (II) and Fe (III) are also candidates due to their high magnetic moments. Once the appropriate metal has been selected, a suitable ligand or chelate must be found to render the complex nontoxic. A number of chelators have been used, including diethylenetriaminepentaacetic (DTPA), 1,4,7,10-tetraazacyclododecane'-N,N'N",N'"-tetracetic acid (DOTA), and derivatives thereof. See WO/1999/025389, U.S. Pat. Nos. 5,155,215, 5,087,440, 5,219,553, 5,188,816, 4,885,363, 5,358,704, 5,262,532, and Meyer et al., Invest. Radiol. 25: S53 (1990).

SUMMARY OF THE INVENTION

The present invention is directed to biocompatible and biodegradable stimuli sensitive polymeric nanoparticles, which may be formed by ion-ion interaction in an aqueous media. The biocompatible and biodegradable nanoparticles of the present invention contain metal ions including a paramagnetic ion moiety, useful as an MRI contrast agent. The nanodevices of the present invention incorporate paramagnetic ions or metals for application as diagnostic contrast agents for Magnetic Resonance Imaging (MRI) and the like.

Biomolecules and their modified derivatives may form stable complexes with paramagnetic ions, thus increasing the molecular relaxivity of carriers. This invention relates to the synthesis of biomolecule-based nanodevices (SBND) for targeted delivery of MRI contrast agents. Nanoparticles (NP's) are constructed by self-assembling chitosan (CHIT) as a polycation and poly-gamma glutamic acid (PGA) as polyanion. NP's are capable of Gd-ion uptake forming a particle with suitable molecular relaxivity. Folic acid (FA) can be linked to the NP's to produce NP-FA bioconjugates that can be used for targeted in vitro delivery to a human cancer cell line.

Macromolecules with ionizable functional groups such as carboxyl, amino, etc., in an aqueous medium form cations and anions, respectively. Under designed conditions of the present invention, polycations and polyanions form nanoparticles by ion-ion interactions. The formation of nanoparticles requires specific reaction parameters, otherwise flocculation and precipitation occurs. However, once the nanoparticles were formed at specific pH's and salt concentrations the nanosystem is stable.

In the present invention, nanoparticles are formed from a reaction whereby polyanions (PA) are complexed with one or more metal ions and the reaction product complex that is formed is coated with a polycation (PC), in aqueous media via ion-ion interaction. The metal ion is preferably a paramagnetic ion (PI). Examples of the metal ion can include Ferric ions, lutetium ions, gold ion, gadolinium ion, chromium ion, dysprosium ion. manganese ion, terbium ion and ferrous ion. The polycation is preferably a polyammonium salt (PAMM) or chitosan. The weight ratio of PA to metal ion is about 10:1-10:5. The chitosan ranges in molecular weight from about 60 kDa to 320 kDa.

The polyanion is preferably selected from a group consisting of polyacrylic acid (PAA), poly-gamma. glutamic acid (PGA), hyaluronic acid (HYAL) and alginic acid (ALGA). The poly gamma glutamic acid can be reacted with carbodiimide and folic acid. In one embodiment, the ion-ion interaction is by means of ionotropic gelation. The weight ratio of chitosan to poly-gamma-glutamic acid is about 1:1.

In an alternate embodiment, the polyanion (PA) is complexed with a metal ion then coated with a polycation (PC) via, for example, ionotropic gelation. A metal ion can be delivered to a cell by reacting a polycation, a metal ion and a polyanion; under conditions sufficient to form polycation-metal ion-polyanion complex and contacting a target cell with the polycation-metal ion-polyanion complex so formed.

DETAILED DESCRIPTION OF THE INVENTION

Sequence of Polyions

Ion-ion interaction can be performed between the functional groups of polyions, and the ratio of original polyions and the order of mixing can affect the sequence of the ion-ion interactions. The linear polyelectrolyte chains can collapse in a compact globule or can extend coil conformations depending on the pH of the reaction solution. The conformation of polymers is a factor in the sequence of polyelectrolyte. Globules of nanoparticles can be formed, where the settlement of polyelectrolytes can be statistical. Core-shell or sandwich-like morphology can be obtained by varying the ratio of original polyions, the pH and the order of mixing.

Figure 1:
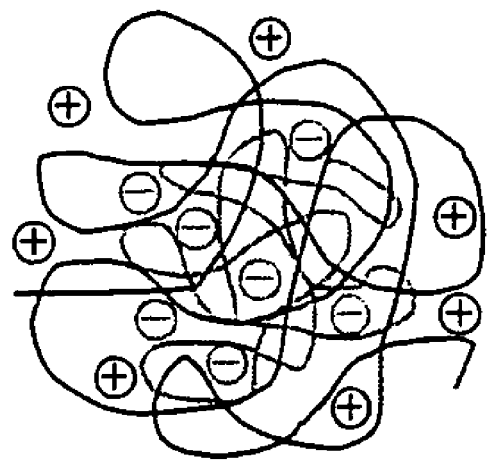
FIGS. 1A and B depicts a representation of nanoparticles formed by ion-ion interaction of polyelectrolyte macromolecules.
Figure 1:
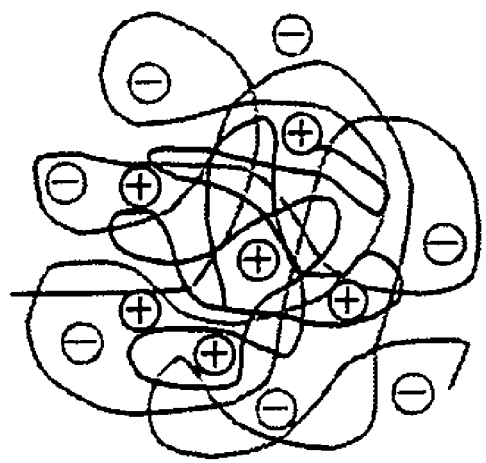

FIGS. 1A and B depicts a representation of nanoparticles formed by ion-ion interaction of polyelectrolyte macromolecules. More specifically, FIG. 1A shows a positively charged polyelectrolyte (dark line) on the surface. FIG. 1B shows a negatively charged polyelectrolyte (light line) on the surface. The surface charge is determined by the sequence of mixing as described below.

Adjusting of pH

The size of nanoparticles depends on the pH of the solution. The hydrodynamic diameter of nanoparticles increases by increasing the pH.

Surface Charge

Surface charge of nanoparticles can show the sequence of polyions. At lower pH, positively charged nanoparticles are typically formed independently of the ratio of polyions or order of mixing. By increasing the pH, negatively charged nanoparticles are formed, which show the charge of polyanions. The ratio of charged free functional groups determines the charge extent of nanoparticles, which depends on the pH and the ratio of functional groups.

Salt Effect

The hydrodynamic diameter and the stability of nanoparticles were investigated in KCl solution. It was found that the hydrodynamic diameters decreased with increasing the salt concentration, but the stability of the aqueous solutions was independent of the salt concentration.

Adjusting the Concentration of Polyions

The stability of the aqueous solution and the size of nanoparticles depend on the original concentration of polyions. The hydrodynamic diameter of nanoparticles increases with increasing the original concentration of polyions. The stability of the aqueous solution decreases with increasing the original concentrations, and precipitation can be observed in some cases of mixing at high concentration of original polyions.

EXAMPLES

Example 1

Nanoparticles Formed from Poly Acrylic Acid (PAA) and Polyammonium Salt (PAMM)

PAA with Mw=200 kDa and poly(2-methacryloxyethyltrimethylammonium bromide) were each separately dissolved in water at a concentration of 1 mg/ml. The pH value of solutions was adjusted to pH=3 by 0.10 mol/dm$^3$ sodium hydroxide. To the solution of PAA under gentile stirring was added the solution of PAMM. After 1 hour the pH was increased to 7 resulting in a stable nanosystem with particle size of 50 to 350 nm measured by laser light scattering method. The size of nanoparticles may be varied and in a range of 10-1,000 nm by using polymers with different molecular weight. Also the particle size increases at higher pH due to the repulsion of negative charges.

Example 2

Nanoparticles Formed from Chitosan (CHIT) and Poly Gamma Glutamic Acid (PGA)

Chitosan is a linear polysaccharide of randomly distributed β-(1-4)-linked D-glucosamine (deacetylated unit) and N-acetyl-D-glucosamine (acetylated unit).

In the present example, CHIT with MW=320 kDa and PGA with Mw=11.3 MDa were each separately dissolved in water. The concentration of the solutions was varied in the range 0.1 mg/ml-2 mg/ml. The pH value of solutions was adjusted to pH=3 by 0.10 mol/dm$^3$ hydrochloric acid. The ratio of polyelectrolyte and the order of mixing was modulated. After 1 hour mixing the pH was increased by 0.1 M sodium hydroxide solution resulting stable nanosystems. The hydrodynamic diameter of nanoparticles was in the range of 40-480 nm at pH=3, and at pH=7 was 470-1300 nm measured by laser light scattering method. There was some precipitation at higher pH caused by flocculation and coagulation. The size of nanoparticles may varied by using polymers with different molecular weight. By increasing the molecular weight of the polymers, the size of the nanoparticles similarly increases.

Example 3

Nanoparticles Formed from CHIT and Hyaluronic Acid (HYAL)

CHIT with Mv=320 kDa and HYAL with Mw=2.5 MDa were dissolved in water. The concentration of CHIT was varied in the range 0.1 mg/ml-1 mg/ml, and of HYAL 0.04-0.2 mg/ml. The pH value of solutions was adjusted to pH=3 by 0.10 mol/dm$^3$ hydrochloric acid. The ratio of polyelectrolyte and the order of mixing was modulated. After 1 hour mixing the pH was increased by 0.1 M sodium hydroxide solution resulting stable nanosystems. The hydrodynamic diameter of nanoparticles was in the range of 130-350 nm at pH=3, and was higher than 600 nm at pH=7 measured by laser light scattering method. There are some precipitation at higher pH caused by flocculation and coagulation.

The size of nanoparticles may varied by using polymers with different molecular weight.

Example 4

Nanoparticles Formed from CHIT and Alginic Acid (ALGA)

CHIT with Mv=320 kDa and ALGA with Mv=30 kDa were dissolved in water. The concentration of CHIT was varied in the range 0.1 mg/ml-1 mg/ml, and of ALGA 0.04-0.2 mg/ml. The pH value of solutions was adjusted to pH=3 by 0.10 mol/dm$^3$ hydrochloric acid. The ratio of polyelectrolyte and the order of mixing was modulated. After 1 hour mixing the pH was increased by 0.1 M sodium hydroxide solution resulting stable nanosystems at a pH=3. There are some precipitation at higher pH caused by flocculation and coagulation.

The size of nanoparticles may varied by using polymers with different molecular weight.

Example 5

Nanoparticles Formed from Modified CHIT and PGA

Chitosan was partially modified by betain. The modification was performed by using carbodiimide technique. CHIT was dissolved in hydrochloric acid media, betaine was dissolved in water and then adjusted the pH to 6.5 with 0.1 M sodium hydroxide solution. Water soluble carbodiimide was added to the betaine solution and the reaction was stirred for 30 min and subsequently mixed with chitosan solution.

The modified CHIT and PGA with Mw=1.3 MDa were dissolved in water. The concentration was varied in the range 0.1 mg/ml-2 mg/ml. The pH value of solutions was adjusted to pH=3 by 0.10 mol/dm$^3$ hydrochloric acid. The ratio of polyelectrolyte and the order of mixing was modulated. After 1 hour mixing the pH was increased by 0.1 M sodium hydroxide solution resulting in stable nanosystems. There is some precipitation at higher pH caused by flocculation and coagulation. The size of nanoparticles may varied by using polymers with different molecular weight.

Example 6

Nanodevice for Targeted Delivery of MRI Contrast Agent

The nanodevice described in Example 2 was modified with paramagnetic ion e.g., gadolinium ion. $Gd^{3+}$ ion forms a complex PGA thus, under magnetic field the relaxation time of water molecules in the environment of nanodevices is different resulting in significant contrast.

We claim:

1. A method of preparing nanoparticles comprising complexing polyanions (PA) with one or more metal ions and coating the complex in aqueous media with polycations (PC) via ion-ion interaction, wherein said polycation is a chitosan that has been reacted with betaine before coating said complex and wherein said chitosan has not been modified before being reacted with said betaine.

2. The method according to claim 1 wherein the metal ion is a paramagnetic ion (PI).

3. The method according to claim 2 wherein the metal ion is a Ferric ion.

4. The method according to claim 2 wherein the metal ion is a Lutetium ion.

5. The method according to claim 2 wherein the metal ion is Gold.

6. The method according to claim 2 wherein the metal ion is a Gadolinium ion.

7. The method according to claim 2 wherein the metal ion is Chromium.

8. The method according to claim 2 wherein the metal ion is a Dysprosium ion.

9. The method according to claim 2 wherein the metal ion is a Manganese ion.

10. The method according to claim 2 wherein the metal ion is a Terbium ion.

11. The method according to claim 2 wherein the metal ion is a Ferro ion.

12. The method of claim 1, wherein said polyanion is selected from a group consisting of polyacrylic acid (PAA), poly-gamma glutamic acid (PGA), hyaluronic acid (HYAL) and alginic acid (ALGA).

13. The method according to claim 1 wherein said ion-ion interaction is by means of ionotropic gellation.

14. The method according to claim 12 wherein said polyanion is poly gamma glutamic acid (PGA).

15. The method according to claim 14 wherein said nanoparticle is conjugated with folic acid.

16. The method according to claim 1 wherein the nanoparticle provides contrast under a magnetic field.

17. The method according to claim 16 wherein the polyanion (PA) is complexed with metal ion then coated with a polycation (PC) via ionotropic gellation.

18. The method according to claim 1 wherein said nanoparticle is used for delivering said one or more metal ions to a cell.

19. The method according to claim 18 wherein the polyanion (PA) is complexed with a metal ion then coated with said polycation (PC), via ionotropic gellation.

20. The method according to claim 18 wherein said one or more metal ions is delivered to said cell by contacting a target cell with said nanoparticle.

21. A method of preparing nanoparticles consisting essentially of complexing poly gamma glutamic acid (PGA) with one or more metal ions; reacting said complex with carbodiimide and folic acid to form a reaction product; and coating said reaction product with a chitosan that has been reacted with betaine, wherein said chitosan has been reacted with betaine before coating said complex, wherein said chitosan has not been modified before being reacted with said betaine, wherein said chitosan component ranges in molecular weight from 60 kDa to about 320 kDa, and wherein said metal ion is selected from the group consisting of Ferric ion, Lutetium ion, Gold, Chromium, Dysprosium ion, Manganese ion, Terbium ion, and Ferro ion.

22. The method according to claim 21 wherein said nanoparticles have a hydrodynamic diameter of from 40 nm to 480 nm at a pH of 3.

23. The method according to claim 21 wherein said nanoparticles have a hydrodynamic diameter of from 470 nm to 1300 nm at a pH of 7.

* * * * *